United States Patent [19]

Schubert et al.

[11] Patent Number: 5,693,628
[45] Date of Patent: Dec. 2, 1997

[54] 11-BENZALDOXIME-ESTRA-DIENE DERIVATIVES, METHODS FOR THEIR PRODUCTION AND PHARMACEUTICALS CONTAINING THESE COMPOUNDS

[75] Inventors: Gerd Schubert; Günther Kaufmann; Lothar Sobeck; Michael Oettel, all of Jena; Walter Elger, Berlin; Anatoli Kurischko, Jena, all of Germany

[73] Assignee: Jenapharm GmbH, Jena, Germany

[21] Appl. No.: 309,175

[22] Filed: Sep. 20, 1994

[51] Int. Cl.⁶ .............................. A61K 31/56; C07J 1/00
[52] U.S. Cl. .............................. 514/179; 552/648
[58] Field of Search .................. 514/177, 179, 514/178; 552/611, 642, 648

[56] References Cited

U.S. PATENT DOCUMENTS

| | | | |
|---|---|---|---|
| 4,829,060 | 5/1989 | Ottow et al. | 514/179 |
| 4,871,724 | 10/1989 | Groen et al. | 514/173 |
| 4,912,097 | 3/1990 | Teutsch et al. | 514/172 |
| 5,089,635 | 2/1992 | Neef et al. | 549/297 |
| 5,272,140 | 12/1993 | Loozen | 514/172 |
| 5,276,023 | 1/1994 | Moguilewsky et al. | 514/179 |
| 5,407,928 | 4/1995 | Kasch et al. | 514/179 |
| 5,576,310 | 11/1996 | Schubert et al. | 514/179 |

FOREIGN PATENT DOCUMENTS

| | | |
|---|---|---|
| 1310630 | 11/1992 | Canada. |
| 2130515 | 3/1995 | Canada. |
| 2130516 | 3/1995 | Canada. |

*Primary Examiner*—Shean C. Wu
*Attorney, Agent, or Firm*—Fliesler, Dubb, Meyer & Lovejoy LLP

[57] ABSTRACT

This invention relates to new 11-benzaldoxime-estra-diene derivatives of the general formula I

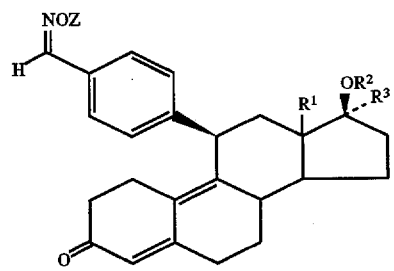

and their pharmaceutically acceptable salts, a method for their production, and pharmaceuticals containing such compounds.

The compounds described show strong antigestagenic effects combined with reduced glucocorticoid activity.

15 Claims, 3 Drawing Sheets

Influence of an antigestagen treatment on the uterine weights of cyclic guinea pigs Antiglucocorticoid effect of J 867 compared with RU 486

Inhibition of CAT induction in the ZR75/AGP-763 line of human mammary cells induced by $10^{-7}$ M dexamethasone.

Antiglucocorticoid effect of J 867 compared with RU 486

Inhibition of TAT induction in the H4 - IIE line of hepatomatous cells of rate induced by $10^{-8}$ M dexamethasone.

2

11-BENZALDOXIME-ESTRA-DIENE DERIVATIVES, METHODS FOR THEIR PRODUCTION AND PHARMACEUTICALS CONTAINING THESE COMPOUNDS

BACKGROUND OF THE INVENTION

1. Field of the Invention

This invention relates to new 11-benzaldoxime-estradiene derivatives, methods for their production, and pharmaceuticals containing these compounds.

2. Description of the Prior Art

11β-substituted phenyl estratrienes are known. Patent specification EP 057 115 describes the production of 11β-aryl-17α-propinyl estra-4,9-dienes, and patent specification DE 3 504 421 describes the reaction of 11β-(4-formyl phenyl)-estra-4,9-diene-3-ons with hydroxylamines. Both the 11β-formyl phenylene residue and the 3-keto group are oximated according to the cited method. In addition, syn and anti isomers are formed at C-3. Nothing is known as yet about the effects of the described compounds.

Progesterone is secreted during menstruation, and in large amounts by the ovary and the placenta during pregnancy. Its regulatory significance has perhaps not been clarified in every respect.

What is safely known is that progesterone, together with oestrogenes, produces the cyclic changes in the uterine mucosa during the menstrual cycle and pregnancy. After ovulation, an increased level of progesterone causes the uterine mucosa to adopt a condition that permits the embedding of an embryo (blastocyst). Conservation of the tissues in which the embryo grows is also dependent on progesterone.

A dramatic change in the muscular function of the uterus takes place during pregnancy. Response of the gravid uterine muscle to hormonal and mechanical stimuli that induce labour in the non-gravid state is strongly reduced or non-existent. There can be no doubt that progesterone has a key function here, despite the fact that at certain stages of pregnancy, e.g. shortly before giving birth, there is a high reactivity even at high blood-progesterone concentrations.

Very high progesterone levels are also reflected by other typical processes during pregnancy. The composition of the mammary glands and the obstruction of the cervix until shortly before the date of birth-giving may serve as examples of this.

Progesterone contributes subtly to controlling ovulation processes. It is known that high doses of progesterone have anti-ovulatory qualities. They result from an inhibition of the hypophyseal gonadotropin secretion which is a prerequisite for the maturation of the follicle and for its ovulation. But on the other hand, it can be seen that the comparatively small quantity of progesterone secreted by the maturing follicle plays an active part in preparing and triggering ovulation. Hypophyseal mechanisms (temporary, so-called positive feedback of progesterone to gonadotropin secretion) appear to have a great significance in this respect (Loutradie, D.; Human Reproduction 6, 1991, 1238–1240).

The doubtlessly existing functions of progesterone in the maturing follicle and luteal corpus themselves have been less well analyzed. It can be assumed, eventually, that there are both stimulating and inhibiting effects on endocrinic functions of the follicle and the luteal corpus.

It may also be assumed that progesterone and progesterone receptors are of great importance for pathophysiological processes. Progesterone receptors have been found in endometriotic focuses, but also in rumours of the uterus, the mamma, and the CNS (meningiomas). The role of these receptors in conjunction with the growth behaviour of these pathologically relevant tissues is not necessarily dependent on progesterone levels in the blood. It has been proved that substances characterized as progesterone antagonists such as RU 486=Mifepristone (EP-0 057 115) and ZK 98299= Onapristone (DE-OS-35 04 421) tend to trigger far-reaching functional changes even at negligible levels of progesterone in the blood. It appears to be possible that modifications of the transcriptional effects of the progesterone receptor that is not filled with progesterone are decisive in this respect (Chwalisz, K. et al., Endocrinology, 129, 317–322, 1991).

The effects of progesterone in tissues of the genitals and in other tissue are brought about by interaction with the progesterone receptor. In a cell, progesterone bonds to its receptor with high affinity. This causes changes in the receptor protein: conformational changes, dimerization of 2 receptor units to form one complex, baring of the receptor's DNA bonding place by dissociating a protein (HSP 90), bonding to hormon-responsive DNA elements. Eventually, the transcription of certain genes is regulated. (Gronemeyer, H. et al., J. Steroid Biochem. Molec. Biol. 41, 3–8, 1992).

The effect of progesterone or progesterone antagonists does not only depend on their concentration in the blood. The concentration of receptors in a cell is strongly regulated as well. Oestrogens stimulate the synthesis of progesterone receptors in most tissues. Progesterone inhibits the synthesis of oestrogen receptors and that of its own receptor. It is assumed that this interaction of oestrogens and gestagens goes to explain why gestagens and antigestagens can influence oestrogen-dependent processes without being bonded by the oestrogen receptor. These relations are naturally of great importance for the therapeutical application of antigestagens. These substances appear to be appropriate for directly influencing female reproductive processes, e.g. for preventing nidation after ovulation, or for increasing uterine reactivity to prostaglandins and oxytocin in a later pregnancy, or for achieving metreurysis and cervix softening ("maturing").

Antigestagens inhibit ovulation in various species of subhuman primates. The mechanism of this effect has not yet been elucidated. Among the hypotheses discussed are an inhibition of gonadotropin secretion, and ovarian mechanisms based on disturbing para- and autocrinic functions of progesterone in the ovary.

Antigestagens are capable of modulating or weakening the effects of oestrogens although the majority of them does not have any oestrogen receptor affinity at the cytoplasmic level, and although they can cause an increase of the oestrogen receptor concentration. Similar effects in endometriotic focuses or tumorous tissue equipped with oestrogen and progesterone receptors justify the expectation of a favourable influence on pathologic conditions. Particular advantages with regard to exerting a favourable influence on pathologic conditions such as endometriosis might be achieved if an inhibited ovulation supplemented the inhibiting effects of an antigestagen acting in the tissue. Ovarian hormonal products and their stimulating effect on the pathologically altered tissue would also be reduced by inhibiting ovulation. It would be desirable to inhibit ovulation in severe cases of endometriosis to bring the tissue in the genital tract which would normally be in constant reconstruction, into a reversible state of rest.

A method is being discussed with regard to contraception according to which an antigestagen treatment suppresses ovulation, and secretory transformation of the endometrium is induced by subsequent gestagen treatment. The days of treatment with antigestagens and gestagens and the treatment-free days result in a 28-day cycle with a regular withdrawal bleeding (Baulieu, E. E., Advances in Contraception 7, 345–51, 1991).

Antigestagens can have different hormonal and anti-hormonal properties. Anti-glucocorticoid properties are of particular therapeutical relevance. These are unfavourable for therapeutical applications mainly aimed at inhibiting progesterone receptors as they have undesired side effects when applied at the dosage required for such therapy which may prevent the application of a therapeutically sensible dose, or require that treatment be discontinued. Partial or complete reduction of anti-glucocorticoid properties is an important prerequisite for a therapy using antigestagens, especially with indications that require therapy over several weeks or months.

SUMMARY OF THE INVENTION

Figure 1:
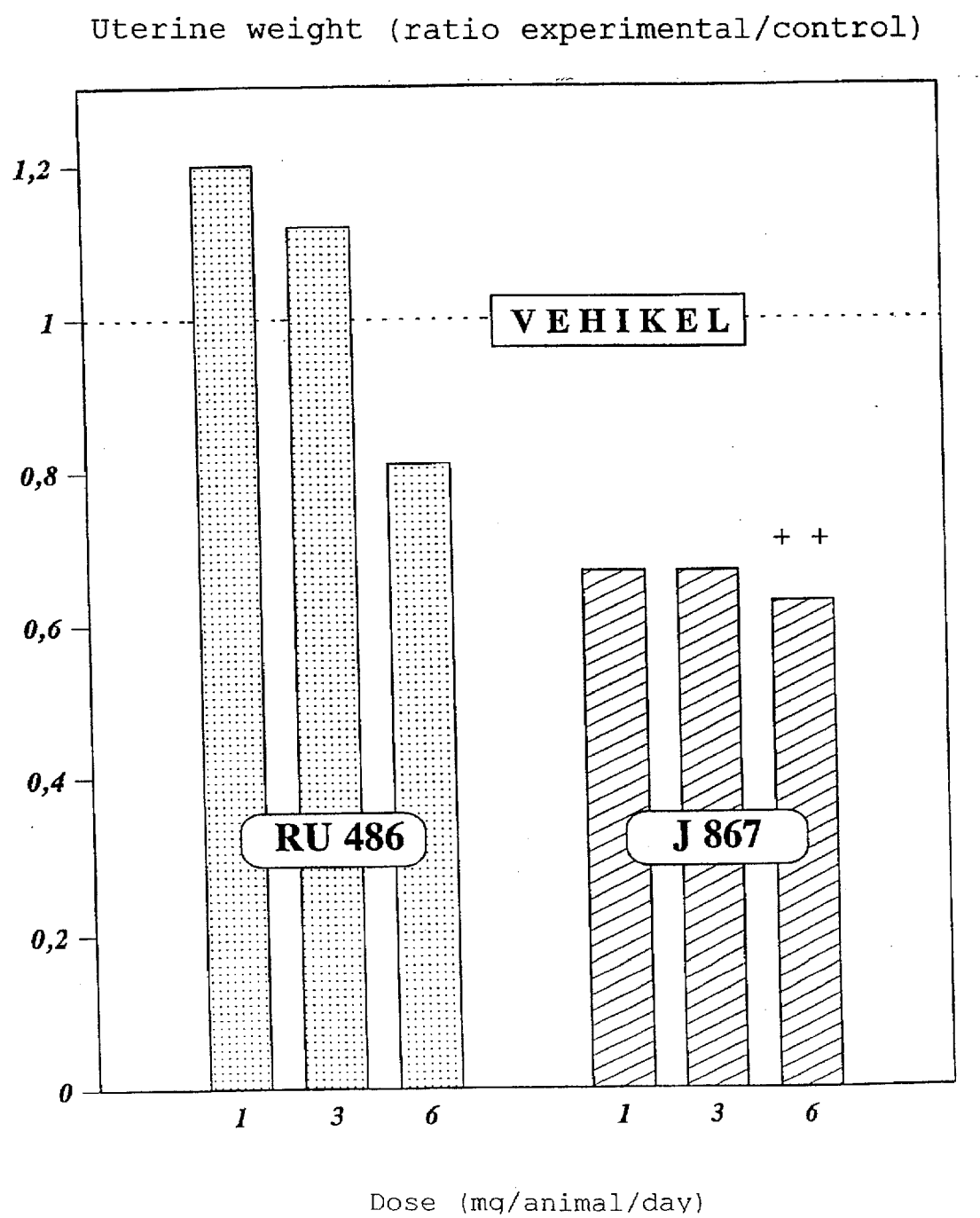
FIG. 1. is a chart showing a comparison of the influence on uterine weight in cyclic guineau pigs when treated with the antigestagen agents RU 486, a control (the vehicle), and a compound of the present invention, J 867 (as prepared in accordance with Example 1). The chart shows dosage in mg/animal/day on the x-axis versus uterine weight ratio (experimental weight versus control weight).

It is the purpose of this invention to provide new 11β-benzaldoxime-estra-4,9-diene derivatives of the general formula I

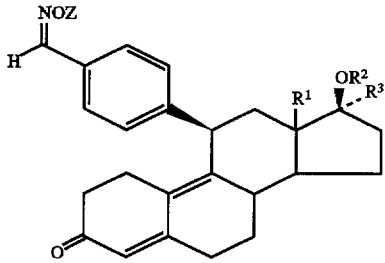

(I)

and its pharmaceutically acceptable salts as well as a method for producing them. It is another purpose of this invention to provide pharmaceuticals containing a compound of the general formula I or its pharmaceutically acceptable salt.

In general formula I,

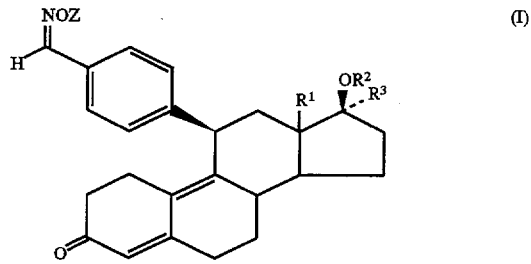

(I)

$R^1$ is a hydrogen atom or alkyl residue containing 1–6 carbon atoms, $R^2$ is a hydrogen atom, an alkyl, aryl, aralkyl, or alkylaryl group containing 1–10 carbon atoms, an acyl residue containing 1–10 carbon atoms, or a residue —CONHR$^4$ or —COOR$^4$, where $R^4$ is a hydrogen atom, an alkyl, aryl, aralkyl, or alkylaryl residue containing 1–10 carbon atoms, $R^3$ is a hydrogen atom, an alkyl, aryl, aralkyl, or alkylaryl group containing 1–10 carbon atoms, a residue —(CH$_2$)$_n$—CH$_2$X, where n=0, 1, or 2, X represents a fluorine, chlorine, bromine, or iodine atom, a cyano, azide, or rhodano group, a residue OR$^5$ or SR$^5$, $R^5$ being a hydrogen atom, an alkyl, aryl, aralkyl, or alkylaryl residue containing 1–10 carbon atoms, or an acyl residue containing 1–10 carbon atoms, a residue OR$^5$, in which $R^5$ has the meaning specified above, a residue —(CH$_2$)$_o$—CH=CH(CH$_2$)$_p$—R$^6$, where o=0, 1, 2, or 3 and p=0, 1, or 2, and R$^6$ represents a hydrogen atom, an alkyl, aryl, aralkyl, or alkylaryl group containing 1–10 carbon atoms, a hydroxyl group, an alkoxy or acyloxy group containing 1–10 carbon atoms, a residue —(CH$_2$)$_q$C≡CR$^7$, where q=0, 1, or 2, and R$^7$ represents a hydrogen atom, a fluorine, chlorine, bromine, or iodine atom, an alkyl, aryl, aralkyl, or alkylaryl residue containing 1–10 carbon atoms, or an acyl residue containing 1–10 carbon atoms, Z represents a hydrogen atom, an alkyl, aryl, aralkyl, or alkylaryl residue containing 1–10 carbon atoms, or an acyl residue containing 1–10 carbon atoms, a residue —CONHR$^4$ or —COOR$^4$, where $R^4$ is a hydrogen atom, an alkyl, aryl, aralkyl, or alkylaryl residue containing 1–10 carbon atoms, or an alkaline or alkaline-earth metal atom.

Preferred are compounds in which $R^1$ is a methyl or ethyl group, $R^2$ represents a hydrogen atom, an alkyl group containing 1–10 carbon atoms, an acyl residue containing 1–10 carbon atoms, or a residue —CONHR$^4$ or —COOR$^4$, where $R^4$ is a hydrogen atom, an alkyl or aryl residue containing 1–10 carbon atoms, $R^3$ is a hydrogen atom, an alkyl, aryl, aralkyl, or alkylaryl group containing 1–10 carbon atoms, $R^3$ is a residue —(CH$_2$)$_n$—CH$_2$X, where n=0, 1, or 2, X represents a fluorine, chlorine, bromine, or iodine atom, a cyano, azide, or rhodano group, a residue OR$^5$ or SR$^5$, R⁵ being an alkyl residue containing 1–6 carbon atoms, or an acyl residue containing 1–6 carbon atoms, a residue OR⁵, R⁵ being a hydrogen atom, an alkyl residue containing 1–10 carbon atoms, or an acyl residue containing 1–10 carbon atoms, a residue —(CH₂)ₒ—CH=CH(CH₂)ₚ—R⁶, where o=0, 1, 2, or 3 and p=0, 1, or 2, and R⁶ represents a hydrogen atom, an alkyl group containing 1–10 carbon atoms, a hydroxyl group, an alkoxy or acyloxy group containing 1–10 carbon atoms, a residue —(CH₂)_qC≡CR⁷, where q=0, 1, or 2, and R⁷ represents a hydrogen atom, a fluorine, chlorine, bromine, or iodine atom, an alkyl residue containing 1–10 carbon atoms, or an acyl residue containing 1–10 carbon atoms, and Z represents a hydrogen atom, an alkyl residue containing 1–10 carbon atoms, an acyl residue containing 1–10 carbon atoms, a residue —CONHR⁴ or —COOR⁴, where R⁴ is a hydrogen atom or an alkyl residue containing 1–10 carbon atoms, or an alkaline or alkaline-earth metal atom.

Particularly preferred are compounds in which R² represents an alkyl group containing 1–6 carbon atoms, an acyl residue containing 1–6 carbon atoms, or a residue —CONHR⁴ or —COOR⁴, where R⁴ is a hydrogen atom or an alkyl or aryl residue containing 1–6 carbon atoms, R³ is a hydrogen atom or an alkyl group containing 1–6 carbon atoms, a residue —(CH₂)ₙ—CH₂X, where n=0, 1, or 2, X represents a fluorine, chlorine, bromine, or iodine atom, a cyano, azide, or rhodano group, a residue OR⁵ or SR⁵, R⁵ being an alkyl residue containing 1–6 carbon atoms, or an acyl residue containing 1–6 carbon atoms, a residue OR⁵, R⁵ being an alkyl residue containing 1–6 carbon atoms, or an acyl residue containing 1–6 carbon atoms, a residue —(CH₂)ₒ—CH=CH(CH₂)ₚ—R⁶, where o=0, 1, 2, or 3 and p=0, 1, or 2, and R⁶ represents an alkyl group containing 1–6 carbon atoms, an alkoxy or acyloxy group containing 1–6 carbon atoms, or a residue —(CH₂)_qC≡CR⁷, where q=0, 1, or 2, and R⁷ represents an alkyl residue containing 1–6 carbon atoms, or an acyl residue containing 1–6 carbon atoms, and Z represents an alkyl residue containing 1–6 carbon atoms, an acyl residue containing 1–6 carbon atoms, a residue —CONHR⁴ or —COOR⁴, where R⁴ is a hydrogen atom, an alkyl or aryl residue containing 1–6 carbon atoms.

Most preferred are:

11β-[4-(hydroximinomethyl)phenyl]-17β-hydroxy-17α-methoxymethyl-estra-4,9-diene-3-on, 11β-[4-(hydroximinomethyl)phenyl]-17β-hydroxy-17α-ethoxymethyl-estra-4,9-diene-3-on, 11β-[4-(hydroximinomethyl)phenyl]-17β-hydroxy-17α-n-propoxymethyl-estra-4,9-diene-3-on, 11β-[4-(hydroximinomethyl)phenyl]-17β-hydroxy-17α-i-propoxymethyl-estra-4,9-diene-3-on, 11β-[4-(hydroximinomethyl)phenyl]-17β-methoxy-17α-methoxymethyl-estra-4,9-diene-3-on, 11β-[4-(hydroximinomethyl)phenyl]-17β-methoxy-17α-ethoxymethyl-estra-4,9-diene-3-on, 11β-[4-(hydroximinomethyl)phenyl]-17β-hydroxy-17α-(3-hydroxyprop-1-in-yl)-estra-4,9-diene-3-on, 11β-[4-(hydroximinomethyl)phenyl]-17β-methoxy-17α-(3-hydroxyprop-1-in-yl)-estra-4,9-diene-3-on, 11β-[4-(hydroximinomethyl)phenyl]-17β-hydroxy-17α-Z-(3-hydroxypropenyl)-estra-4,9-diene-3-on, 11β-[4-(hydroximinomethyl)phenyl]-17β-methoxy-17α-Z-(3-hydroxypropenyl)-estra-4,9-diene-3-on, 17α-chloromethyl-11β-[4-(hydroximinomethyl)phenyl]-17β-hydroxy-estra-4,9-diene-3-on, 17α-chloromethyl-11β-[4-(hydroximinomethyl)phenyl]-17β-methoxy-estra-4,9-diene-3-on, 17α-cyanomethyl-11β-[4-(hydroximinomethyl)phenyl]-17β-hydroxy-estra-4,9-diene-3-on, 17α-cyanomethyl-11β-[4-(hydroximinomethyl)phenyl]-17β-methoxy-estra-4,9-diene-3-on, 17α-azidomethyl-11β-[4-(hydroximinomethyl)phenyl]-17β-methoxy-estra-4,9-diene-3-on, 11β-[4-(hydroximinomethyl)phenyl]-17β-methoxy-17α-methylthiomethyl-estra-4,9-diene-3-on, 11β-[4-(methyloximinomethyl)phenyl]-17β-methoxy-17α-methoxymethyl-estra-4,9-diene-3-on, 11β-[4-(acetoximinomethyl)phenyl]-17β-methoxy-17α-methoxymethyl-estra-4,9-diene-3-on, 11β-[4-(methyloximinomethyl)phenyl]-17β-hydroxy-17α-methoxymethyl-estra-4,9-diene-3-on, 11β-{4-[(ethoxycarbonyl)oximinomethyl]phenyl}-17β-methoxy-17α-methoxymethyl-estra-4,9-diene-3-on, 11β-{4-[(ethylaminocarbonyl)oximinomethyl]phenyl}-17β-methoxy-17α-methoxymethyl-estra-4,9-diene-3-on, 17β-methoxy-17α-methoxymethyl-11β-{4-[(phenylaminocarbonyl)oximinomethyl]phenyl}-estra-4,9-diene-3-on, and 11β-[4-(hydroximinomethyl)phenyl]-17β-ethoxy-17α-ethoxymethyl-estra-4,9-diene-3-on.

This invention furthermore relates to a method for producing compounds of the general formula I and their pharmaceutically acceptable salts, characterized in that a compound of the general formula II (II)

wherein R¹, R², and R³ have the abovementioned meanings, is reacted with a compound of the general formula IIa NH₂—O—Y                                                  (IIa)

where Y is a hydrogen atom, an alkyl residue containing 1–10 carbon atoms, an acyl residue containing 1–10 carbon atoms, or a residue —CONHR⁴ or —COOR⁴, where R⁴ represents a hydrogen atom, an alkyl, aryl, aralkyl, or alkylaryl residue containing 1–10 carbon atoms, and where the compound of the general formula IIa is present, in the form of such compound, or in a form from which the compound of the general formula IIa is released under the selected conditions of the reaction, the hydroxyl amine group, if present, is esterified or etherified, and the resulting compound is optionally salified.

Compounds of the general formula II preferably react with compounds of the general formula IIa if the compounds are added in equimolar quantities.

If esterification, etherification or urethane formation is desired, and if their R² or Z substituent is a hydroxyl group, compounds of the general formula I may further be treated as follows: esterification in a generally known way using acylating agents such as acid anhydrides or acid chlorides in the presence of bases, preferably pyridine, etherification using methyl iodide in the presence of bases, preferably potassium tert. butanolate; urethane formation by reacting with alkyl or aryl isocyanates in inert solvents, preferably toluene, or by reacting carbamoylchlorides in the presence of bases, preferably triethylamine.

The parent compound of the general formula II is manufactured from 5α,10α-epoxide III

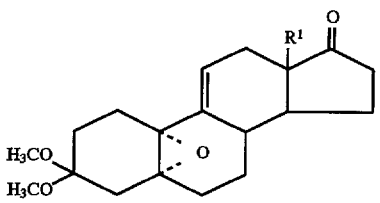

[cf., for example, Nédélec Bull. Soc. chim. France 1970), 2548].

Introduction of the phenyl residue to the 11β position while forming a Δ9(10),5α hydroxy structure IV is achieved by a Cu(I) salt catalyzed Grignard reaction (Tetrahedron Letters 1979, 2051) with a p-bromobenzaldehyde ketal, preferably p-bromobenzaldehyde dimethyl ketal at temperatures between 0° C. and 30° C.

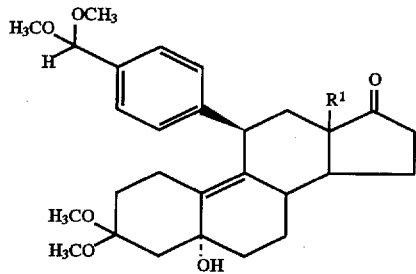

The —(CH₂)ₙCH₂X group is introduced in a generally known way via the spiroepoxide V by reacting with trimethyl sulfonium iodide and potassium tert. butanolate in dimethyl sulfoxide [Hübner et al.; J. prakt. Chem. 314, 667 (1972); Arzneim. Forsch. 30, 401 (1973)] and

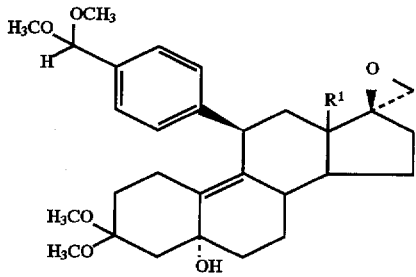

subsequent ring opening using nucleophiles such as halogenides and pseudohalogenides, alcoholates and mercaptides [Ponsold et al.; Z. Chem. 11, 106 (1971)]. The resulting 17α-CH₂X compounds VI

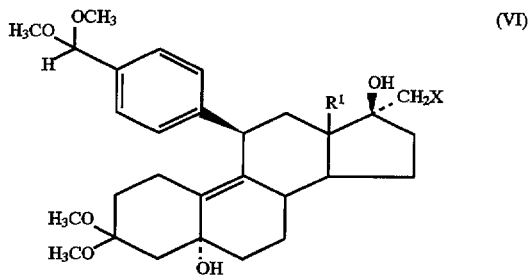

may either be decomposed into aldehydes of the general formula II with R² being a hydrogen atom by acid hydrolysis, preferably using toluene-p-sulfonic acid in acetone (Teutsch et al. DE 2801416), or be converted, following etherification of the free hydroxyl groups with alkyl halogenides in the presence of potassium tert. butanolate, first into 5α,17β diethers (Kasch et al. DD 290 893) which are then transformed into aldehydes of the general formula II with R² being alkyl residues, preferably a methyl residue, by acid hydrolysis, preferably using toluene-p-sulfonic acid in acetone.

The —(CH₂)ₒ—CH=CH(CH₂)ₚ—R⁶ residues are introduced by reacting the ketone IV with propyn-1-ol-tetrahydropyranyl ether and potassium tert. butanolate to obtain the 17α-(3-hydroxy-1-propinyl)-17β-hydroxy compounds VII,

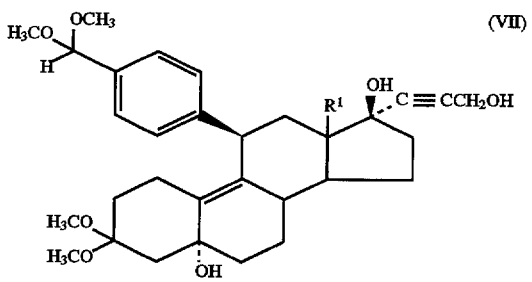

which may either be hydrolyzed by acid hydrolysis under the conditions specified above to become aldehydes of type II with R² being a hydrogen atom, or, after forming the 5α,17β diethers, be hydrolyzed according to the abovementioned procedure with subsequent acid hydrolysis to yield aldehydes of type II with R² being an alkyl residue, or be hydrated in a generally known reaction using deactivated catalysts such as 10% palladium on barium sulfate in the presence of an amine to become 17α-(3-hydroxypropenyl) -17β-hydroxy compounds that also convert into type II aldehydes after acid hydrolysis.

The —(CH₂)ᵩC≡CR⁷ residues are introduced in the known way by reacting the ketone IV with acetylene, propyn or higher homologues in the presence of alkaline metals such as lithium, sodium or potassium in connection with an alcohol or ammonia, or with butyl lithium in ethers such as tetrahydrofurane. Acid hydrolysis of these compounds results in the 17α-C≡CR⁷-substituted aldehydes of type II.

The resulting compound of the general formula I according to the invention is converted, if required, into an acid addition salt, preferably a salt of a physiologically compatible acid. Common physiologically compatible anorganic and organic acids are, for example, hydrochloric acid, hydrobromic acid, phosphoric acid, sulfuric acid, oxalic acid, maleic acid, fumaric acid, lactic acid, tartaric acid, malic acid, citric acid, salicylic acid, adipic acid, and benzoic acid. Other acids that can be used are described, for example, in *Fortschritte der Arzneimittelforschung*, vol. 10, pp. 224–225, Birkhäuser Verlag, Basel and Stuttgart, 1966, and Journal of Pharmaceutical Sciences, vol. 66, pp. 1–5 (1977).

Acid addition salts are normally obtained in a generally known way by mixing the free base or its solutions with the respective acid or its solutions in an organic solvent, for example, a lower alcohethanol, n-methanol, ethanol, n-propanol or isopropanol, or a lower ketone such as acetone, methylethyl ketone or methyl isobutyl ketone, or an ether such as diethyl ether, tetrahydrofurane or dioxane. Compositions of the abovementioned solvents may be used for improved crystallizing. In addition, physiologically compatible hydrous solutions of acid addition salts of the compound according to formula I may be produced in a hydrous acidic solution.

The acid addition salts of compounds of the general formula I can be converted into a free base in a generally known way, e.g. using alkalies or ion exchangers. Other salts can be obtained by reacting this free base with anorganic or organic acids, especially acids suited for forming pharmaceutically acceptable salts. These and other salts of the new compound, such as its picrate, may be used to purify the free base: the free base is converted into a salt, the salt is separated, and the base released from the salt again.

Another object of this invention are pharmaceuticals designed for oral, rectal, subcutaneous, intravenous or intramuscular applications that contain as an active ingredient, apart from the usual substrates and diluents, a compound according to the general formula I or its acid addition salt.

The pharmaceuticals of the invention are produced in a known way using the usual solid or liquid substrates or diluents and the common adjuvants used in pharmaceutical engineering and with an appropriate dosage depending on the intended mode of application. Preferred formulations are those forms suitable for oral administration, for example, tablets, film tablets, dragées, capsules, pills, powder, solutions, suspensions, or depot forms.

Consideration may be given also to parenteral formulations such as injection solutions. Suppositories represent another form of application.

Tablets may be obtained, for example, by intermixing the active substance with known adjuvants, for example, inert diluents such as dextrose, sugar, sorbitol, mannite, polyvinylpyrrolidone, blasting agents such as maize starch or alginic acid, binders such as starch or gelatin, lubricants such as magnesium stearate or talcum and/or materials by which to produce a depot effect, such as carboxyl polymethylene, carboxymethyl cellulose, cellulose acetate phthalate or polyvinyl acetate. Tablets may consist of several layers.

Dragées may be produced accordingly by coating cores manufactured in analogy to tablet manufacture using agents generally applied to dragée coating, for example, polyvinylpyrrolidone or shellac, Arabic gum, talcum, titanium dioxide, or sugar. The coating of the dragée may also consist of several layers in which the adjuvants mentioned in the paragraph on tablets can be used.

Solutions or suspensions containing the active agent of the invention may additionally contain flavour-enhancing substances such as saccharin, cyclamate or sugar, or aromatic substances such as vanillin or orange extract. They may also contain suspension-supporting adjuvants such as sodium carboxymethyl cellulose, or preservatives such as p-hydroxybenzoates. Capsules containing active substances may be produced, for example, by mixing the active substance with an inert substrate such as lactose or sorbitol, and encapsulating such mixture in gelatin capsules.

Appropriate suppositories may be made by mixing the active substance with the suitable substrates, such as neutral fats or polyethylene glycol and their derivatives.

Figure 2:
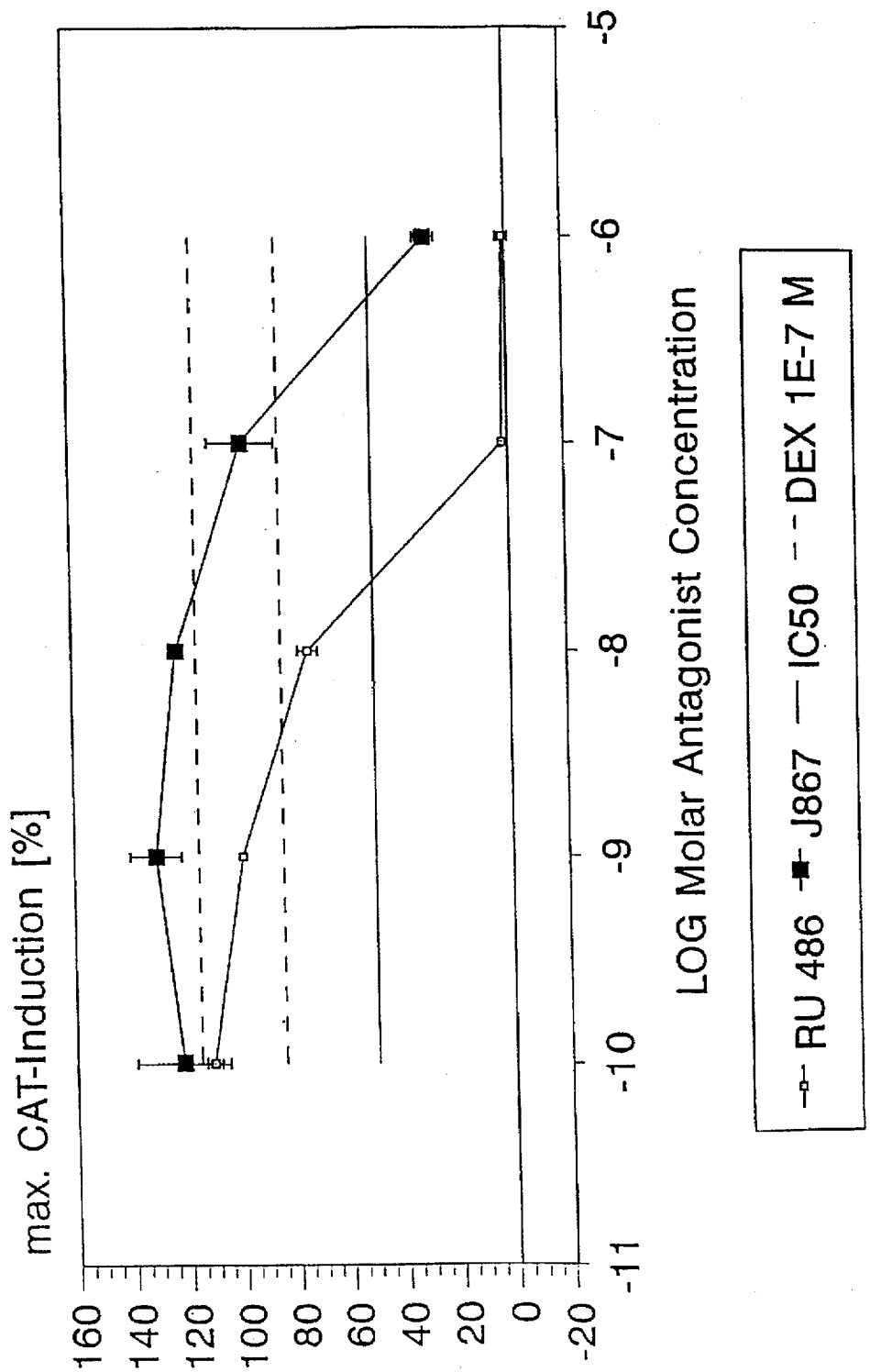
FIG. 2. is a graph showing the antiglucocorticoid effect of J 867 (Example 1) in comparison to RU 486. The graph depicts the inhibition of CAT induction in a human mammary cell line (the ZR75/AGP-763 cell line) which were induced by $10^{-7}$M dexamethasone. The graph indicates the log molar antagonist concentration in the x-axis versus the maximum CAT induction as a percentage in the y-axis. The results for dexamethasone is shown as dashed lines (- - -), the IC50 is shown in solid line (——), RU 486 is shown as open boxes (□), and J 867 is shown with closed boxes (■).
Figure 3:
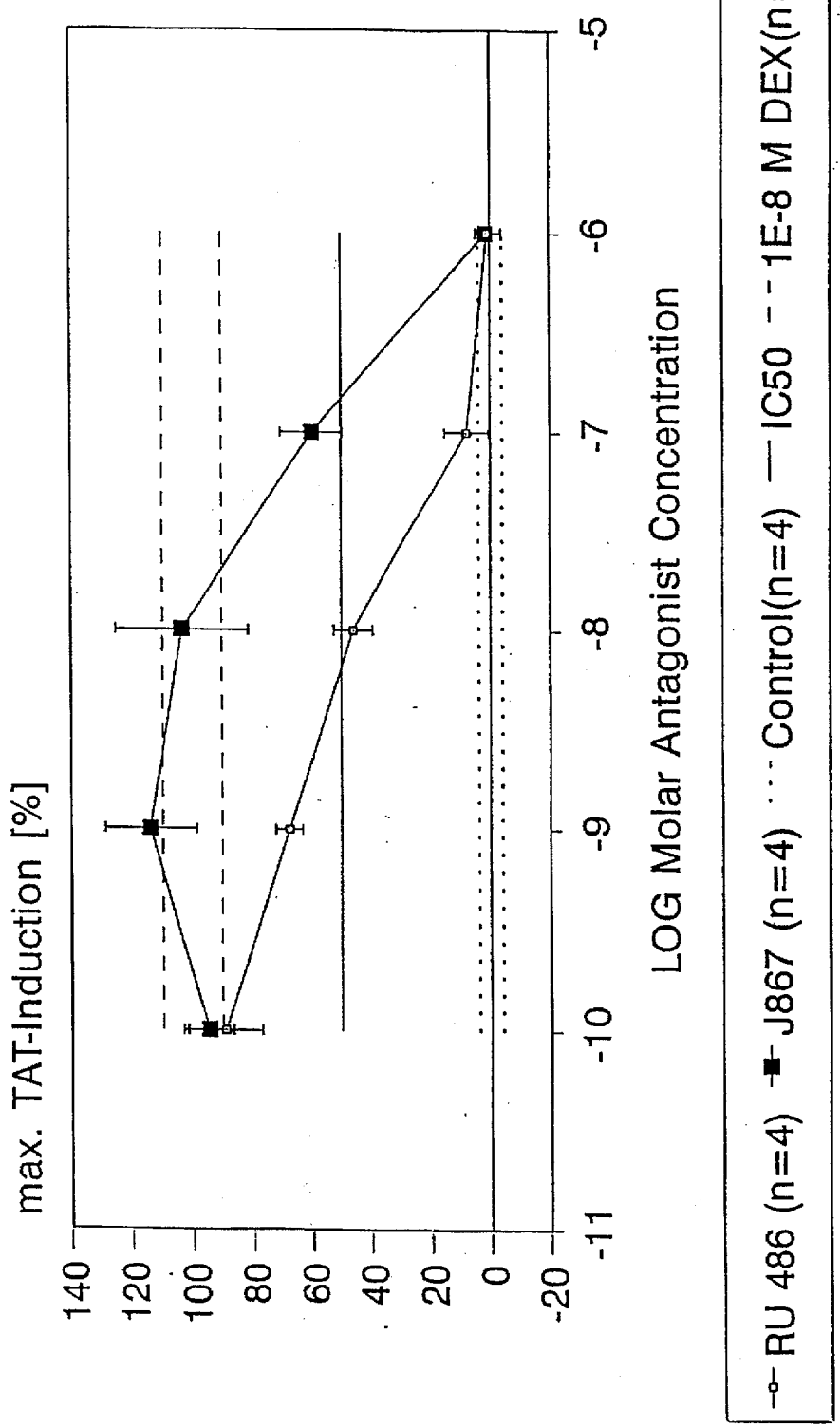
FIG. 3. is a graph showing the antiglucocorticoid effect of J 867 (Example 1) in comparison to RU 486. The graph depicts the inhibition of TAT induction in a rat hepatoma cell line (the H4-IIE cell line) which were induced by $10^{-8}$M dexamethasone. The graph indicates the log molar antagonist concentration in the x-axis versus the maximum TAT induction as a percentage in the y-axis. The results for dexamethasone is shown as dashed lines (- - -), the IC50 is shown in solid line (——), RU 486 is shown as open boxes (□), and J 867 is shown with closed boxes (■).

The 11β-substituted benzaldoxime-estra-4,9-dienes of the invention are antigestagenic substances that show the same activity at the progesterone receptor as RU 486 (Mifepristone) (cf. table 1) and a superior in-vivo effect (cf. FIG. 1 and table 2) while at the same time having a clearly reduced antiglucocorticoid activity which has been proved by the diminished bonding to the gluco-cortinoid receptor (cf. table 1) as well as by the decreased inhibition of enzyme induction in lines of cells which is by one power of ten lower (cf. FIGS. 2 and 3).

TABLE 1

Receptor of selected substances listed in Examples 1 to 5

| Compound acc. to example | relative molar bonding affinity (RBA) [%] to | | |
|---|---|---|---|
| | progesterone receptor (progesterone = 100%) | glucocorticoid receptor (dexamethasone = 100%) | oestrogen rec. (estradiol = 100%) |
| 1 (J867) | 302 | 78 | <0.1 |
| 2 | 136 | 82 | <0.1 |
| 3 | 236 | 73 | <0.1 |
| 4 | 294 | 66 | <0.1 |
| 5 | 90 | 32 | <0.1 |
| compared with | | | |
| RU 486 (Mifepristone) | 506 | 685 | |
| ZK 98299 (Onapristone) | 22 | 39 | |

Selected antigestagens of the invention (J 687) produce significantly reduced uterine weights in the anovulatorial cycle in guinea pigs at doses at which RU 486 increases uterine weights as compared with control animals.

This combination of properties of the antigestagen according to the invention promises superior inhibition of progesterone while at the same time reducing antiglucocorticoid activity.

This advantage is of particular relevance for indications that require excellent compatibility because of the duration of treatment. During the menstrual cycle, uterine weight is decisively influenced by the circulating oestrogen. Reduced uterine weights reflect an inhibition of this oestrogenic function. The inhibition of uterine weight during the menstrual cycle determined in guinea pigs is superior to RU 486 and points to (indirect) anti-oestrogenic properties of the compounds according to the invention. The respective effects promise the exertion of a particularly favourable influence on pathologically modified tissues in which oestrogens stimulate growth (endometriotic focuses, myomas, mammary and genital carcinomas, benign prostatic hypertrophy).

TABLE 2

Early abortive effect of RU 486 and J 867 (Example 1) in the rat after subcutaneous application from the 5th to 7th day of pregnancy (dose 0.2 ml/animal/day in benzyl benzoate/castor oil [1 + 4 v/v])

| Group, substance | Dose (mg/animal/ day) | complete gravidity inhibition[+] N*/N | % | ED 50[++] (mg/animal/ day) |
|---|---|---|---|---|
| vehicle | — | 0/13 | 0 | — |
| RU 486 | 3.0 | 5/5 | 100 | 1.3 |
|  | 1.0 | 2/5 | 40 |  |
|  | 0.3 | 0/5 | 0 |  |
| J 867 | 3.0 | 5/5 | 100 | 0.6 |
|  | 1.0 | 5/5 | 100 |  |
|  | 0.3 | 0/5 | 0 |  |

[+]empty uteri
N number of inseminated females
N* number of females not pregnant
[++]graphic determination FIG. 1 compares the influence of antigestagen treatment of cyclic guinea pigs on uterine weights for J 867 and RU 486.

High doses of RU 486 (6 mg/24 hrs) reduce the uterine weights of the treated animals. A low dosis of this substance, however, results in a slight gain in uterine weights. All doses of J 867 tested (1, 3, and 6 mg/24 hrs) inhibited uterine weights to a statistically significant extent.

FIG. 2 depicts the antiglucocorticoid effect produced by J 867 in the ZR 75/AGP-763 line of human mammary cells compared with that of RU 486.

In this cell line, dexamthasone induces the chloroamphenicol acetyl transferase gene (CAT). This induction is inhibited by antiglucocorticoid substances. Surprisingly, J 867 inhibits CAT over a wide range of concentrations to a lesser extent than RU 486 (Mifepristone).

FIG. 3 compares the antiglucocorticoid effect of J 867 and RU 486 on hepatomatous cells of rats using the TAT model.

In hepatomatous cells of rats, dexamethasone stimulates the tyrosine amino transferase enzyme (TAT). This effect is inhibited by antiglucocorticoid activity. J 867 apparently has a clearly weaker antiglucocorticoid effect than RU 486.

The following examples explain the present invention.

EXAMPLES

Example 1

434 mg of 11β-(4-formylphenyl)-17β-methoxy-17α-methoxymethyl-estra-4,9-diene-on are dissolved at room temperature in 8 ml of pyridine; then 65 mg of hydroxylamine hydrochloride are added, and the batch is agitated at 25° C. Another 5 mg of hydroxylamine hydrochloride are added after 2 hours. After 15 minutes, the solution is diluted with water, added with 1N of aqueous hydrochloric acid, and extracted with chloroform. The organic phase is washed with dilute HCl and water and dried above sodium sulfate and potassium carbonate. The solvent is evaporated under reduced pressure. Yield: 420 mg of crude product. After adding acetone, crystals precipitate that are filtered off by suction and recrystallized from isopropanol/$CH_2Cl_2$.

Yield: 305 mg of 11β-[4-(hydroximinomethyl)phenyl]-17β-methoxy-17α-methoxymethyl-estra-4,9-diene-3-on.

Melting point: 118° C. with decomposition $\alpha_D$=+197° ($CHCl_3$)

IR spectrum in $CHCl_3$ ($cm^{-1}$): 3575, 3300 (OH); 1705 (C=NOH); 1649 (C=C—C=C—C=O); 1599 (phenyl)

UV spectrum in MeOH: $\lambda_{max}$=264 nm $\epsilon$=20 366 $\lambda_{max}$=299 nm $\epsilon$=20 228

$^1$H-NMR spectrum in $CDCl_3$ [δ, ppm]: 0.533 (s, 1H, H-18); 3.252 (s, 3H, 17β-OC$\underline{H}_3$); 3.393 (s, 3H, 17α-CH$_2$OC$\underline{H}_3$); 3.441–3.598 (m, 2H, ABX system of C$\underline{H}_2$OR); 4.381 (d, 1H, J=6.9 Hz, H-11α); 5.788 (s, 1H, H-4); 7.187–7.487 (m, 4H, AA'BB' system of aromatics protons); 8.05 (s, 1H, OH); 8.097 (s, 1H, C$\underline{H}$=NOH)

MS m/e: 449.25509 $C_{29}H_{35}NO_4$ $M^+$

Manufacturing of the parent compound:

Step A 50 g of 4-bromobenzaldehyde and 30 ml of o-triethyl formate are agitated for 5 hours at room temperature in 60 ml of methanol and 0.8 ml of thionyl chloride. After that, another 0.2 ml of thionyl chloride are added. The batch is poured into aqueous bicarbonate solution after 30 minutes and extracted with chloroform, washed with aqueous bicarbonate solution and water, dried above sodium sulfate, and concentrated by evaporation under reduced pressure. 68 g of 4-bromobenzaldehyde dimethyl ketal are obtained in the form of colourless oil.

0.2 ml of dibromomethane are added to 2.3 g of magnesium in 20 ml of anhydrous THF with argon as inert gas. When the reaction starts, 21.96 g of 4-bromobenzaldehyde dimethyl ketal in 70 ml of anhydrous THF are dripped in in such a way that the temperature does not rise above 40° C. After the whole amount has been added, the batch is agitated for 2 hours at 30° C., then cooled down to –10° C. 511 mg of CuCl are added. Agitation is continued at –30° C. for 15 more minutes. Then, a solution of 6 g of 3,3-dimethoxy-5α,10α-epoxy-estr-9,11-en-17-on in 30 ml of anhydrous THF is dripped in. The batch is allowed to warm up to room temperature. The Grignard solution is decomposed using an aqueous solution of ammonium chloride. The product is isolated by extracting with acetic ester. The organic phase is washed neutrally and dried above sodium sulfate. After the solvent has been removed by distillation under reduced pressure, 19.7 g of crude product are obtained.

Chromatography using 300 g of silica gel and 20 g of aluminium oxide with a toluene/acetic ester gradient yields 7.38 g of 3,3-dimethoxy-11β-[4-(dimethoxymethyl)phenyl]-5α-hydroxy-estr-9-en-17-on in the form of a yellow foam.

Step B 10.38 g of trimethyl sulfonium iodide and 7.64 g of (portioned) potassium tert. butanolate are added to 7.38 g of 3,3-dimethoxy-11β-[4-(dimethoxymethyl)phenyl]-5β-hydroxy-estr-9-en-17-on dissolved in 85 ml dimethylsulfoxide using argon as inert gas. After 1.5 hours and cooling down to 0°–5° C., aqueous ammonium chloride solution is added. The sticky precipitate is extracted with $CH_2Cl_2$, washed neutrally, dried above sodium sulfate, and isolated in the form of brown resin after the solvent has been evaporated.

Yield: 8.63 g of 3,3-dimethoxy-11β-[4-(dimethoxymethyl)phenyl]-17β-spiro-1',2'-oxirane-estr-9-en-5α-ol.

Step C 20 ml of a 3N sodium methylate solution are added to 8.63 g of 3,3-dimethoxy-11β-[4-(dimethoxymethyl)phenyl]-17β-spiro-1',2'-oxirane-estr-9-en-5α-ol dissolved in 20 ml of methanol, and refluxed for 2–3 hours. The solvent is evaporated under reduced pressure, the remainder is taken up in $CH_2Cl_2$, and washed neutrally. The solution is dried above sodium sulfate and evaporated under reduced pressure.

Yield: 8.74 g of crude product in the form of a brown foam. Chromatography using 260 g of silica gel and 90 g of aluminium oxide in a toluene/acetic ester gradient yields 1.92 g of 3,3-dimethoxy-11β-[4-(dimethoxymethyl)phenyl]-17α-methoxymethyl-estr-9-en-5α,17β-diol.

Step D 8.65 g of potassium tert. butanolate are added in the presence of inert gas to 1.92 g of 3,3-dimethoxy-11β-[4-(dimethoxymethyl)phenyl]-17α-methoxymethyl-estr-9-en-5α, 17β-diol in 120 ml of toluene. The suspension is agitated for 5 minutes at room temperature. Then 6.35 ml of methyl iodide in 6 ml of toluene are dripped in in such a way that the temperature does not rise above 40° C. 20 ml of water and 20 ml of acetic ester are added after one hour, and the phases are separated. The watery phase is extracted with acetic ester. The organic phase is washed neutrally, dried above sodium sulfate, and evaporated under reduced pressure.

Yield: 1.55 g of 3,3-dimethoxy-11β-[4-(3,3-dimethoxymethyl)phenyl]-17α-methoxymethyl-estr-9-en-5α,17β-dimethyl ether in the form of a yellow foam.

Step E 1.55 g of 3,3-dimethoxy-11β-[4-(3,3-dimethoxymethyl) phenyl]-17α-methoxymethyl-estr-9-en-5α,17β-dimethyl ether are dissolved in 12.6 ml of acetone; 1.3 ml of water are added. 158 mg of 4-toluene sulfonic acid are added in the presence of inert gas. The batch is agitated for 40 minutes at room temperature. The crystal pulp is filtered off by suction, washed with acetone, and crystallized from $CH_2Cl_2$/acetone.

Yield: 0.55 g of colourless crystals.

Recrystallizing from $CH_2Cl_2$/acetone yields 440 mg of 11β-(4-(formylphenyl)-17β-methoxy-17α-methoxymethyl-estra-4,9-diene-3-on.

Melting point: 233°–240° C.

$α_D$=+189° (CHCl$_3$)

IR spectrum in CHCl$_3$ (cm$^{-1}$): 1710 (CHO); 1660 (C=C—C=C—C=O); 1610 (phenyl)

UV spectrum in MeOH: $λ_{max}$=262 nm $ε$=10 775 $λ_{max}$= 299 nm $ε$=13 999

$^1$H-NMR spectrum in CDCl$_3$ [δ, ppm]: 0.48 (s, 3H, H-18); 3.25 (s, 3H, 17β-OCH$_3$); 3.38 (s, 3H, 17α-CH$_2$OCH$_3$); 4.40 (d, 1H, J=7.2 Hz, H-11α); 5.78 (s, 1H, H-4); 7.28–7.93 (m, 4H, AA'BB' system of aromatics protons); 9.95 (s, 1H, CHO)

MS m/e: 434.24771 C$_{28}$H$_{34}$O$_4$ M$^+$

Example 2

217 mg of 11β-(4-(formylphenyl)-17β-methoxy-17α-methoxymethyl-estra-4,9-diene-3-on in 4 ml of pyridine and 40 mg of methoxyamine hydrochloride are agitated at room temperature. Another 5.2 mg of methoxyamine hydrochloride are added after one hour. 10 ml of water and 10 ml of acetic ester are added, the phases separated, the aqueous phase re-extracted, the organic phase washed in 10 ml of dilute HCl and neutrally in distilled water, dried, and evaporated under reduced pressure. 241 mg of crude product in the form of a resin are obtained. Preparative thin-layer chromatography using silica gel 60 PF$_{254+366}$ and a toluene/acetone solvent system at a concentration of 4:1 yields 188 mg of the product in the form of a foam.

Recrystallization from acetone/hexane provides 11β-[4-(methoximinomethyl)phenyl]-17β-methoxy-17α-methoxymethyl-estra-4,9-diene-3-on in the form of colourless lamellae.

Melting point: 83°–89° C.

$α_D$=+179° (CHCl$_3$)

IR spectrum in CHCl$_3$ (cm$^{-1}$): 1700 (C=NOCH$_3$); 1649 (C=C—C=C—C=O); 1590 (aromatic)

UV spectrum in MeOH: $λ_{max}$=275 nm $ε$=23 098 $λ_{max}$= 300 nm $ε$=22 872

$^1$H-NMR spectrum in CDCl$_3$ [δ, ppm]: 0.529 (s, 3H, H-18); 3.247 (s, 3H, 17β-OCH$_3$); 3.408 (s, 3H, 17α-CH$_2$OCH$_3$); 3.39–3.598 (m, 2H, ABX system, 17α-CH$_2$OCH$_3$); 4.381 (d, 1H, J=7.5 Hz, H-11α); 5.773 (s, 1H, H-4); 7.173, 7.201, 7.463, 7.491 (m, 4H, AA'BB' system of aromatics protons); 8.023 (s, 1H, CHphenyl)

MS m/e: 463.26950 C$_{29}$H$_{37}$NO$_4$ M$^+$

Example 3

180 mg of 11β-[4-(hydroximinomethyl)phenyl]-17β-methoxy-17α-methoxymethyl-estra-4,9-diene-3-on are acetylated in 12 hours in 5 ml of acetic anhydride/pyridine (1:1). After adding water, the batch is three times extracted with acetic ester. The organic phase is washed with dilute hydrochloric acid and water, dried above sodium sulfate, and concentrated by evaporation under reduced pressure. The yield is 172 mg of crude product that is purified by preparative thin-layer chromatography using silica gel PF$_{245+366}$ and a toluene/acetone solvent system at a concentration of 4:1.

Yield: 115 mg of 11β-[4-(acetyloximinomethyl)phenyl]-17β-methoxy-17α-methoxymethyl-estra-4,9-diene-3-on. The product crystallizes from acetic ester.

Melting point: 115°–120° C. (acetic ester)

$α_D$=+218° C. (CHCl$_3$)

UV spectrum in MeOH: $λ_{max}$=271 nm $ε$=28 157 $λ_{max}$= 297 nm $ε$=26 369

$^1$H-NMR spectrum in CDCl$_3$ [δ, ppm]: 0.511 (s, 3H, H-18); 2.227 (s, 3H, OCOCH$_3$); 3.247 (s, 3H, 17β-OCH$_3$); 3.408 (s, 3H, 17α-CH$_2$OCH$_3$); 3.386, 3.431, 3.544, 3.580 (m, 2H, CH$_2$OCH$_3$); 4.399 (d, 1H, J=7.2 Hz, H-11α); 5.785 (s, 1H, H-4); 7.242, 7.266, 7.618, 7.647 (m, 4H, AA'BB' system of aromatics protons); 8.315 (s, 1H, CH=NOAc)

MS m/e: 491.26971 C$_{30}$H$_{37}$NO$_5$ M$^+$

Example 4

0.3 ml of chloroethyl formate are dripped into 210 mg of 11β-[4-(hydroximinomethyl)phenyl]-17β-methoxy-17α-methoxymethyl-estra-4,9-diene-3-on in 5 ml of pyridine while cooling with water. A white sediment forms. The batch is watered after 30 minutes, which results in a solution in which a white sediment settles down that is filtered off by suction and washed in water. Yield after drying: 133 mg. The aqueous phase is extracted with chloroform, washed with dilute hydrochloric acid and water, dried, and concentrated by evaporation under reduced pressure. Yield: 66 mg. Both solids are united and purified by preparative thin-layer chromatography using silica gel 60 PF$_{245+366}$ and a toluene/acetone solvent system at a concentration of 4:1.

Yield: 150 mg of 11β-{4-[ethoxycarbonyl)oximinomethyl]-phenyl}-17β-methoxy-17α-methoxymethyl-estra-4,9-diene-3-on which are recrystallized from acetone/hexane.

Melting point: 137°–148° C. (decomposition)

$α_D$=+204° (CHCl$_3$)

UV spectrum in MeOH: $λ_{max}$=270 nm $ε$=27 094 $λ_{max}$=297 nm $ε$=25 604

$^1$H-NMR spectrum in CDCl$_3$ [δ, ppm]: 0.507 (s, 3H, H-18); 1.383 (t, 3H, J=7.0 Hz, OCH$_2$CH$_3$); 3.246 (s, 3H, 17β-OCH$_3$); 3.410 (s, 3H, 17α-CH$_2$OCH$_3$); 3.39–3.56 (m, 2H, CH$_2$OCH$_3$); 4.35 (d, 1H, J=7.0 Hz, H-11α); 5.784 (s, 1H, H-4); 7.23, 7.26, 7.61, 7.64 (m, 4H, AA'BB' system of aromatics protons); 8.303 (s, 1H, CH=NR)

MS m/e: 431.24701 $C_{28}H_{33}NO_3$ $M^+$—$C_2H_5OCOOH$

Example 5

244 mg of 11β-(4-formylphenyl)-17β-hydroxy-17α-chloromethyl-estra-4,9-diene-3-on in 4 ml of pyridine and 32.2 mg of hydroxylamine hydrochloride are agitated at room temperature. Another 6.9 mg of hydroxylamine hydrochloride are added after 1 hour. 10 ml of water and 10 ml of acetic ester are added, the phases separated, the aqueous phase re-extracted, the organic phase washed in 10 ml of dilute HCl and neutrally in distilled water, dried, and evaporated under reduced pressure.

183 mg of crude product in the form of a yellow resin are obtained. Preparative thin-layer chromatography using silica gel 60 $PF_{254+366}$ and a toluene/acetone solvent system at a concentration of 4:1 yields 87.7 mg of 17α-chloromethyl-11β-[4-(hydroxyiminomethyl)phenyl]-17β-hydroxy-estra-4,9-diene-3-on, in the form of a foam.

$\alpha_D=+185°$ (CHCl$_3$)

UV spectrum in MeOH: $\lambda_{max}$=264 nm $\epsilon$=20 797 $\lambda_{max}$= 299 nm $\epsilon$=20 439

$^1$H-NMR spectrum in CDCl$_3$ [δ, ppm]: 0.607 (s, 3H, H-18); 3.628, 3.664, 3.824, 3.861 (m, 2H, ABX system, 17α-C$\underline{H}_2$Cl); 4.428 (d, 1H, J=6.9 Hz, H-11α); 5.807 (s, 1H, H-4); 7.185, 7.212, 7.482, 7.509 (m, 4H, AA'BB' system of aromatics protons); 8.05 (s, 1H, OH); 8.104 (s, 1H, C$\underline{H}$phenyl).

MS m/e: 439.19070 $C_{26}H_{30}ClNO_3$ $M^+$

Manufacturing of the parent compound
Step F 16.6 ml of concentrated HCl are slowly dripped into 4.12 g of 3,3-dimethoxy-11β-[4-(dimethoxymethyl)phenyl]-17β-spiro-1',2'-oxirane-estr-9-en-5α-ol (manufactured according to example 1, step B) in 84 ml of dimethyl formamide at 0° C. 420 ml of water are stirred in after one hour, by which a white sediment is formed. The mixture is set to pH 6 using an aqueous bicarbonate solution, the sediment is filtered off by suction and dried.

Yield of crude product: 3.38 g of ochre-coloured crystals that are purified by column chromatography on 90 g of silica gel 60 using a toluene/acetic ester gradient.

Yield: 1.16 g of 17α-chloromethyl-11β-(4-formylphenyl)-17 β-hydroxy-estra-4,9-diene-3-on in the form of crystals.

Melting point: 205°-208° C. (acetone/hexane)

$\alpha_D=+161°$ (CHCl$_3$)

IR spectrum in CHCl$_3$ (cm$^{-1}$): 3600 (OH); 1695 (CHO); 1650 (C=C—C=C—C=C); 1590 (phenyl)

UV spectrum in MeOH: $\lambda_{max}$=262 nm $\epsilon$=19 993 $\lambda_{max}$= 297 nm $\epsilon$=22 755

$^1$H-NMR spectrum in CDCl$_3$ [δ, ppm]: 0.583 (s, 3H, H-18); 3.30 (s, 1H, OH); 3.63–3.85 (m, 2H, ABX system of C$\underline{H}_2$Cl); 4.45 (d, 1H, J=7.0 Hz, H-11α); 5.809 (s, 1H, H-4); 7.355, 7.382, 7.799, 7.826 (m, 4H, AA'BB' system of aromatics protons); 9.977 (s, 1H, C$\underline{H}$O)

MS m/e: 424.18280 $C_{26}H_{29}ClO_3$ $M^+$

Example 6

136 mg of 11β-(4-formylphenyl)-17β-hydroxy-17α-methoxymethyl-estra-4,9-diene-3-on are dissolved at room temperature in 2.2 ml of pyridine; then 18 mg of hydroxylamine hydrochloride are added, and the batch is agitated at 25° C. Another 4 mg of hydroxylamine hydrochloride are added after 1.5 hours. After 15 minutes, the solution is diluted with water, added with 1N of aqueous HCl, and extracted with chloroform. The organic phase is washed with dilute HCl and water and dried above sodium sulfate and potassium carbonate. The solvent is evaporated under reduced pressure.

Yield: 146 mg of crude product that is purified by preparative thin-layer chromatography using silica gel 60 $PF_{254+366}$ and a toluene/acetone solvent system at a concentration of 4:1.

Yield: 110 mg of 11β-[4-(hydroxyiminomethyl)phenyl]-17β-hydroxy-17α-methoxymethyl-estra-4,9-diene-3-on.

Melting point: 104° C. with decomposition (isopropanol)

$\alpha_D=+195°$ (CHCl$_3$)

UV spectrum in MeOH: $\lambda_{max}$=263 nm $\epsilon$=21 170 $\lambda_{max}$= 299 nm $\epsilon$=20 188

$^1$H-NMR spectrum in CDCl$_3$ [δ, ppm]: 0.517 (s, 1H, H-18); 3.418 (s, 3H, 17α-CH$_2$OC$\underline{H}_3$); 3.206, 3.237, 3.552, 3.582 (m, 2H, ABX system of C$\underline{H}_2$OCH$_3$); 4.384 (d, 1H, J=7.2 Hz, H-11α); 5.784 (s, 1H, H-4); 7.179, 7.206, 7.456, 7.483 (m, 4H, AA'BB' system of aromatics protons); 7.9 (s, 1H, OH); 8.088 (s, 1H, C$\underline{H}$=NOH).

MS m/e: 435.24289 $C_{27}H_{33}NO_4$ $M^+$

Manufacturing of the parent compound
Step G 860 mg of 3,3-dimethoxy-11β-[4-(dimethoxymethyl)phenyl]-17α-methoxymethyl-estr-9-en-5α,17β-diol (manufactured according to Step C of Example 1) are dissolved in 80 ml of acetone. After adding 7.7 ml of water and 430 mg of 4-toluene sulfonic acid, the batch is refluxed for 1.5 hours and concentrated by evaporation under reduced pressure. The remainder is taken up in chloroform and set to pH 8 using 8 ml dilute ammonia. Phases are separated. The organic phase is washed neutrally, dried above sodium sulfate, and evaporated under reduced pressure.

590 mg of 11β-(formylphenyl)-17β-hydroxy-17α-methoxymethyl-estra-4,9-diene-3-on-1 as crude product are obtained and recrystallized from acetic ester.

Melting point: 195°-205° C. (acetic ester)

$\alpha_D=+209°$ (chloroform)

IR spectrum in CHCl$_3$ (cm$^{-1}$): 3590 (OH); 1710 (CHO); 1660 (C=C—C=C—C=O); 1605 (aromatic)

UV spectrum in MeOH: $\lambda_{max}$=263 nm $\epsilon$=20 683 $\lambda_{max}$= 298 nm $\epsilon$=20 749

$^1$H-NMR spectrum in CDCl$_3$ [δ, ppm]: 0.509 (s, 3H, H-18); 2.666 (s, 1H, OH); 3.196, 3.226, 3.550, 3.580 (m, 2H, ABX system of C$\underline{H}_2$OCH$_3$); 3.417 (s, 3H, OC$\underline{H}_3$); 4.446 (d, 1H, J=6.9 Hz, H-11α); 5.797 (s, 1H, H-4); 7.360, 7.386, 7.786, 7.813 (m, 4H, AA'BB' system of aromatics protons); 9.970 (s, 1H, C$\underline{H}$O)

MS m/e: 420.23300 $C_{27}H_{32}O_4$ $M^+$

Example 7

480 mg of 17α-ethoxymethyl-11β-(4-formylphenyl)-17β-methoxy-estra-4,9-diene-3-on are dissolved at room temperature in 6 ml of pyridine; then 74 mg of hydroxylamine hydrochloride are added, and the batch is agitated at 25° C. Another 8.5 mg of hydroxylamine hydrochloride are added after 30 minutes. After 15 minutes, the solution is diluted with water, added with 1N of aqueous HCl, and extracted with CH$_2$Cl$_2$. The organic phase is washed with dilute HCl and water and dried above sodium sulfate and potassium carbonate. The solvent is evaporated under reduced pressure.

Yield: 410 mg of crude product that yields 230 mg of 17α-ethoxymethyl-11β-[4-(hydroxyiminomethyl)phenyl]-17β-methoxy-estra-4,9-diene-3-on in the form of a yellow foam after preparative thin-layer chromatography using silica gel 60 $PF_{254+366}$.

$\alpha_D$=+200° (CHCl$_3$)

UV spectrum in MeOH: $\lambda_{max}$=264 nm $\epsilon$=20 366 $\lambda_{max}$= 299 nm $\epsilon$=20 228

$^1$H-NMR spectrum in CDCl$_3$ [δ, ppm]: 0.533 (s, 1H, H-18); 1.267 (t, 3H, J=6.9 Hz, 17α-CH$_2$OCH$_2$CH$_3$); 3.252 (s, 3H, 17 β-OCH$_3$); 3.423–3.623 (m, 2H, ABX system, 17α-CH$_2$OCH$_2$CH$_3$); 4.355 (d, 1H, J=7.2 Hz, H-11α); 5.783 (s, 1H, H-4); 7.191, 7.219, 7.460, 7.488 (m, 4H, AA'BB' system of aromatics protons); 8.097 (s, 1H, CH=NOH).

MS m/e: 463.27069 C$_{29}$H$_{37}$NO$_4$ M$^+$

Manufacturing of the parent compound

Step H 5.33 g of 3,3-dimethoxy-11β-[4-(dimethoxymethyl) phenyl]-17β-spiro-1',2'-oxirane-estr-9-en-5α-ol (manufactured according to Step B of Example 1) are dissolved in 5 ml of ethanol, 25 ml of 1.5N sodium ethylate solution are added, and the batch is refluxed for one hour. The solvent is evaporated under reduced pressure and the remainder taken up in CH$_2$Cl$_2$ and washed neutrally. The solution is dried above sodium sulfate and evaporated under reduced pressure.

5.85 g of crude product are obtained in the form of a brown foam. Chromatography on silica gel using a toluene/ acetic ester gradient yields 1.14 g of 3,3-dimethoxy-11β-[4-(dimeth-oxymethyl)phenyl]-17α-ethoxymethyl-estr-9-en-5α,17β-diol.

Step I 5.14 g potassium tert. butanolate are added to 1.14 g of 3,3-dimethoxy-11β-[4-(dimethoxymethyl)phenyl]-17α-ethoxymethyl-estr-9-en-5α,17β-diol in 70 ml of toluene, using argon as protective gas. A mixture of 3.8 ml methyl iodide in 4 ml toluene are dripped in after 15 minutes. The reaction is interrupted after 2 hours by adding 20 ml of water and 20 ml of acetic ester. The organic phase is washed twice with water, dried above sodium sulfate, and evaporated under reduced pressure.

Yield of crude product: 1.14 g of 3,3-dimethoxy-11β-[4-(3,3-dimethoxymethyl)phenyl]-17α-ethoxymethyl-17β-methoxy-estr-9-en-5α-ol.

Step J 116 mg 4-toluene sulfonic acid and 1 ml of water are added to 1.14 g of 3,3-dimethoxy-11β-[4-(dimethoxymethyl)phenyl]-17α-ethoxymethyl-17β-methoxy-estr-9-en-5α-ol in 10 ml of acetone, using a protective gas. After 30 minutes, the batch is diluted with water and twice extracted with acetic ester. The organic phase is washed and dried above sodium sulfate. 900 mg of 17α-ethoxymethyl-11β-(4-formylphenyl)-methoxy-estra-4,9-diene-3-on remain as yellow foam after evaporating the solvent. Chromatography on silica gel 60 with a toluene/ acetic ester gradient yields 480 mg of yellow crystals.

Example 8

244 mg of 11β-(4-formylphenyl)-17β-hydroxy-17α-(3-hydroxy-prop-1-in-yl)-estra-4,9-diene-3-on are dissolved at room temperature in 4.5 ml of pyridine; then 35.5 mg of hydroxylamine hydrochloride are added, and the batch is agitated at 25° C. Another 4.8 mg of hydroxylamine hydrochloride are added after 30 minutes. After 15 minutes, the solution is diluted with water, taken up in acetic ester, and extracted by shaking with 1N aqueous hydrochloric acid. The organic phase is washed with water and dried above sodium sulfate and potassium carbonate. The solvent is evaporated under reduced pressure. Yield: 216 mg of crude product. This crude product yields 192 mg of 11β-[4-(hydroximinomethyl) phenyl]-17β-hydroxy-17α-(3-hydroxyprop-1-in-yl)-estra-4,9-diene-3-one as a colourless foam after preparative thin-layer chromatography on silica gel 60 PF$_{254+366}$ using toluene/acetone (4:1) as a solvent system.

Melting point: 171°–179° C. (ether)

$\alpha_D$=+82° (dioxane)

UV spectrum in MeOH: $\lambda_{max}$=264 nm $\epsilon$=21 495 $\lambda_{max}$= 299 nm $\epsilon$=20 236

MS m/e: 445.22369 C$_{28}$H$_{31}$NO$_4$ M$^+$

Manufacturing of the parent compound

Step K 12 ml of 15% n-butyl lithium in hexane are dripped into 3 ml of prop-in-yl-3-hydroxytetrahydropyranyl ether in 27 ml of anhydrous THF at −5° C. After 15 minutes, 1.2 g of 3,3-dimethoxy-11β-[4-(dimethoxymethyl)phenyl]-5α-hydroxy-estr-9-en-17-on (manufactured according to Step B in Example 1) in 16 ml of anhydrous THF are added to this solution by dripping. The batch is agitated for 30 minutes at room temperature. The reaction mixture is poured into 150 ml of iced water and extracted with acetic ester. The organic phase is washed neutrally, dried above sodium sulfate, and evaporated under reduced pressure.

4.23 g of a brown oil are obtained that are purified by chromatography on silica gel 60 with a toluene/acetic ester gradient. The yield is 422 mg of 3,3-dimethoxy-11β-[4-(dimethoxymethyl)phenyl]-17α-(3-tetrahydropyranyloxyprop-1-in-yl)-estr-9-en-5α,17β-diol in the form of a foam.

Step L 540 mg of 3,3-dimethoxy-11β-[4-(dimethoxymethyl) phenyl]-17α-(3-tetrahydropyranyloxyprop-1-in-yl)-estr-9-en-5α,17β-diol are agitated for 2 hours at room temperature in 40 ml of acetone together with 100 mg of 4-toluene sulfonic acid. Then the batch is concentrated by evaporation to 10 ml, added with aqueous sodium bicarbonate solution, and extracted with acetic ester. The organic phase is washed neutrally, dried above sodium sulfate, and evaporated under reduced pressure.

Yield of crude product: 330 mg. Purifying by preparative thin-layer chromatography on silica gel 60 PF$_{254+366}$ yields 310 mg of 11β-(4-formylphenyl)-17β-hydroxy-17α-(3-hydroxy-prop-1-in-yl)-estra-4,9-diene-3-on. Recrystallization from acetone provides white crystals.

Melting point: 225°–231° C.

$\alpha_D$=+59° (chloroform)

UV spectrum in MeOH: $\lambda_{max}$=302 nm $\epsilon$=23 608

$^1$H-NMR spectrum in CDCl$_3$ [δ, ppm]: 0.496 (s, 3H, H-18); 4.375 (s, 2H, C—CH$_2$OH); 4.497 (d, 1H, J=7.2 Hz, H-11α); 5.810 (s, 1H, H-4); 7.353, 7.380, 7.797, 7.824 (m, 4H, AA'BB' system of aromatics protons); 9.974 (s, 1H, C HO)

MS m/e: 430.21460 C$_{28}$H$_{30}$O$_4$ M$^+$

Example 9

190 mg of 11β-[4-(hydroximinomethyl)phenyl]-17β-methoxy-17α-methoxymethyl-estra-4,9-diene-3-on are suspended in 10 ml of toluene. 0.5 ml of phenyl isocyanate and 1 ml of triethyl amine are added subsequently. The batch is agitated at room temperature for 3 hours and refluxed for 2 hours. The white sediment is filtered off by suction, and the solvent concentrated by evaporation under reduced pressure. Thus 310 mg of a light brown solid are obtained which is purified by preparative thin-layer chromatography using silica gel 60 PF$_{254+366}$ and a toluene/acetone solvent system at a concentration of 9:1.

65 mg of 17β-methoxy-17α-methoxymethyl-11β-{4-[(phenylamino-carbonyl)oximinomethyl]phenyl}-estra-4,9-diene-3-on are isolated.

Melting point: 241°–246° C. (acetone)

$\alpha_D = +178°$ (CHCl$_3$)

UV spectrum in MeOH: $\lambda_{max}$=238 nm $\epsilon$=29 444 $\lambda_{max}$= 300 nm $\epsilon$=29 649

$^1$H-NMR spectrum in CDCl$_3$ [$\delta$, ppm]: 0.474 (s, 3H, H-18); 3.245 (s, 3H, 17$\beta$-OCH$_3$); 3.405 (s, 3H, 17$\alpha$-CH$_2$OCH$_3$); 3.406–3.545 (m, 2H, ABX system, 17$\alpha$-CH$_2$OCH$_3$); 4.413 (d, J=6.8 Hz, 1H, H-11$\alpha$); 5.797 (s, 1H, H-4); 7.264 (m, 5H, aromatic); 7.272, 7.293, 7.548, 7.575 (m, 4H, AA'BB' system of aromatics protons); 8.0 (s, 1H, CH=N—)

MS m/e: 431.24249 C$_{28}$H$_{33}$NO$_3$ M$^+$—C$_6$H$_5$CNO+H$_2$O

Example 10

125 mg of 17$\alpha$-ethoxymethyl-11$\beta$-(4-formylphenyl)-17$\beta$-hydroxy-estra-4,9-diene-3-on are dissolved at room temperature in 2 ml of pyridine; then 20.2 mg of hydroxylamine hydrochloride are added, and the batch is agitated at 25° C. After 50 minutes, the solution is diluted with water, acetic ester is added, and the phases are separated. The organic phase is washed with dilute HCl and water and dried above sodium sulfate. The solvent is evaporated under reduced pressure.

127 mg of crude product in the form of a bright yellow foam are obtained that yield 62 mg of 17$\alpha$-ethoxymethyl-11$\beta$-[4-(hydroximinomethyl)phenyl]-17$\beta$-hydroxy-estra-4,9-diene-3-on in the form of a colourless foam after preparative thin-layer chromatography using silica gel 60 PF$_{254+366}$.

$\alpha_D = +226°$ (CHCl$_3$)

UV spectrum in MeOH: $\lambda_{max}$=265 nm $\epsilon$=22 696 $\lambda_{max}$= 299 nm $\epsilon$=21 960

$^1$H-NMR spectrum in CDCl$_3$ [$\delta$, ppm]: 0.520 (s, 1H, H-18); 1.249 (t, 3H, J=7.2 Hz, 17$\alpha$-CH$_2$OCH$_2$CH$_3$); 3.228–3.609 (m, 4H, 2×CH$_2$); 4.381 (d, 1H, J=7.2 Hz, H-11$\alpha$); 5.781 (s, 1H, H-4); 7.181, 7.209, 7.459, 7.486 (m, 4H, AA'BB' system of aromatics protons); 8.098 (s, 1H, CH=NOH).

MS m/e: 449.25540 C$_{28}$H$_{35}$NO$_4$ M$^+$

Manufacturing of the parent compound

Step M 340 mg 3,3-dimethoxy-11$\beta$-[4-(dimethoxymethyl)phenyl]-17$\alpha$-ethoxymethyl-estr-9-en-5$\alpha$,17$\beta$-diol (manufactured according to Step H in Example 7) are dissolved in 2.5 ml of acetone. 0.25 ml of water and 35 mg of 4-toluene sulfonic acid are added. After 1 hour, the batch is diluted with 10 ml of water, and 10 ml of acetic ester are added. The phases are separated. The aqueous solution is twice re-extracted, the organic solution is washed and dried above sodium sulfate. After evaporating the solvent, 300 mg of yellowish crystals remain.

200 mg of 17$\alpha$-ethoxymethyl-11$\beta$-(4-formylmethyl)-17$\beta$-hydroxy-estra-4,9-diene-3-on in the form of yellowish crystals are obtained after preparative thin-layer chromatography on silica gel 60 PF$_{254+366}$ with toluene/acetone (9:1).

Melting point: 144°–150° C. (acetone/hexane)

$\alpha_D = +171°$ (CHCl$_3$)

UV spectrum in MeOH: $\lambda_{max}$=263 nm $\epsilon$=17 842 $\lambda_{max}$= 299 nm $\epsilon$=20 083

$^1$H-NMR spectrum in CDCl$_3$ [$\delta$, ppm]: 0.512 (s, 1H, H-18); 1.249 (t, 3H, $\Sigma$J=4.6 Hz, 17$\alpha$-CH$_2$OCH$_2$CH$_3$); 3.221–3.613 (m, 4H, 2×CH$_2$); 4.447 (d, 1H, J=6.9 Hz, H-11$\alpha$); 5.799 (s, 1H, H-4); 7.361, 7.388, 7.788, 7.816 (m, 4H, AA'BB' system of aromatics protons); 9.972 (s, 1H, CH=O).

Example 11

Measurement of bonding affinity for receptors

Receptor bonding affinity was determined by competitive bonding of a specifically binding $^3$H labelled hormone (tracer) and the compound to be tested to receptors in the cytosol from animal target organs. It was tried to obtain receptor saturation and a balanced reaction. The following incubation conditions were selected:

Progesterone receptor: uterine cytosol of the estradiol-primed rabbit, kept at −30° C. in TED buffer (20 mM Tris/HCl, pH 7.4; 1 mM ethylene diamine tetraacetate, 2 mM dithio threitol) with 250 mM of saccharose. Tracer: $^3$H-ORG 2058, 5 nM; reference substance: progesterone.

Glucocorticoid receptor: thymus cytosol of the adrenalectomized rat, thymi kept at −30° C., buffer: TED. Tracer: $^3$H-dexamethasone, 20 nM; reference substance: dexamethasone.

Oestrogen receptor: uterine cytosol of the immature rabbit, kept at −30° C. in TED buffer with 250 mM of saccharose. Tracer: $^3$H-ethinyl estradiol, 3 nM; reference substance: 17$\beta$-estradiol.

After an incubation period of 18 hours at 0°–4° C., bonded and free steroid was separated by mixing in active carbon/dextrane (1%/0.1%), centrifuging off and measuring the bonded $^3$H activity in the supernatant.

The IC$_{50}$ for the compound to be tested and for the reference substance were determined from measurements in series of concentrations. The quotient of both values (×100%) is the relative molar bonding affinity.

Example 12

Inhibition of early gravidity in the rat

Female rats are mated in the pro-oestrus. If semen is found in the vaginal smear on the next day, this day is counted as day 1 (=d1) of the gravidity. Treatment with the test substance or vehicle is applied on d5–d7, autopsy is carried out on d9. The substances are injected subcutaneously in 0.2 ml of vehicle (benzyl benzoate/castor oil 1+4). The rate of fully inhibited gravidities found in various groups can be seen from table 1. An inhibition capability of nidation was found for J 867 to be superior by a factor of 3 as compared to RU 486.

Example 13

Treatment of female guinea pigs with antigestagen

Treatment of adult female guinea pigs from day 10 to day 18 of the cycle (autopsy). Administration of the specified doses using subcutaneous osmotic pumps (Type 2 ML1 ALZET). Vehicle: 2.0 ml propylene glycol/24 hrs.

Example 14

Antiglucocorticoid effect of J867 in the ZR75/AGP-763 line of human mammary cells The cell culture experiments were carried out in RPMI 1640 added with 10% foetal calf serum (FCS) using an incubator cabinet containing 95% air and 5% CO$_2$ at 37° C. The cells were spread in 60 mm Petri dishes. The medium of the confluent cells was replaced by a medium containing 5% FCS (treated with dextrane coated charcoal, DCC). Dexamethasone at a concentration of 10$^{-7}$M in ethanol (0.2%; v/v) was added to induce CAT. The stimulated cells were harvested 16 hours later by producing a cell extract with a cellysis buffer. CAT was determined using a Boehringer ELISA according to the instructions for quantitative CAT determination of transfected cells.

Example 15

Antiglucocorticoid effect of J867 in hepatomatous cells of rats using the TAT model The cell cultures were treated in DMEM under essentially the same conditions as in Example 14. The cells were spread over 24 well plates for the experiments. Substance was added to the confluent hepatomatous cells in 0.2% (v/v) ethanol for 16 hours. After the cells were carefully harvested using a scraper and a cell extract obtained using ultrasonic waves, TAT was determined according to Diamondstone.

What we claim is:

1. 11β-benzaldoxime-estra-4,9-diene-derivatives of the general formula I:

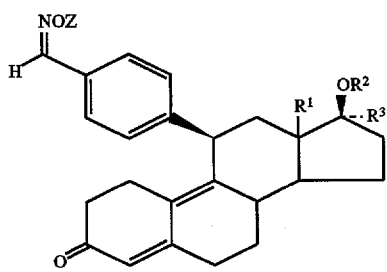

Formula I wherein $R^1$ is selected from the group consisting of a hydrogen atom or alkyl residue containing 1–6 carbon atoms, $R^2$ is selected from the group consisting of a hydrogen atom, an alkyl, aryl, aralkyl, or alkylaryl group containing 1–10 carbon atoms, an acyl residue containing 1–10 carbon atoms, or a residue —$CONHR^4$ or —$COOR^4$, where $R^4$ is selected from the group consisting of a hydrogen atom, an alkyl, aryl, aralkyl, or alkylaryl residue containing 1–10 carbon atoms, $R^3$ is selected from the group consisting of a hydrogen atom, an alkyl, aryl, aralkyl, or alkylaryl group containing 1–10 carbon atoms, a residue —$(CH_2)_n$—$CH_2X$, where n=0, 1, or 2, X is selected from the group consisting of a fluorine, chlorine, bromine, or iodine atom, a cyano, azido, or rhodano group, a residue $OR^5$ or $SR^5$, $R^5$ being a hydrogen atom, an alkyl, aryl, aralkyl, or alkylaryl residue containing 1–10 carbon atoms, or an acyl residue containing 1–10 carbon atoms, a residue $OR^5$, in which $R^5$ has the meaning specified above, a residue —$(CH_2)_o$—$CH=CH(CH_2)_p$—$R^6$, where o=0, 1, 2, or 3 and p=0, 1, or 2, and $R^6$ is selected from the group consisting of a hydrogen atom, an alkyl aryl, aralkyl, or alkylaryl group containing 1–10 carbon atoms, a hydroxy group, an alkoxy or acyloxy group containing 1–10 carbon atoms, a residue —$(CH_2)_q C \equiv CR^7$, where q=0, 1, or 2, and $R^7$ is selected from the group consisting of a hydrogen atom, a fluorine, chlorine, bromine, or iodine atom, an alkyl, aryl, aralkyl, or alkylaryl residue containing 1–10 carbon atoms, or an acyl residue containing 1–10 carbon atoms, Z is selected from the group consisting of a hydrogen atom, an alkyl, aryl, aralkyl, or alkylaryl residue containing 1–10 carbon atoms, or an acyl residue containing 1–10 carbon atoms, a residue —$CONHR^4$ or —$COOR^4$, where $R^4$ is selected from the group consisting of a hydrogen atom, an alkyl, aryl, aralkyl, or alkylaryl residue containing 1–10 carbon atoms, or an alkaline or alkaline-earth metal atom, and pharmaceutically acceptable salts thereof;

with the exception of compounds wherein $R^2$ is —$CH_3$, $R^3$ is —$CH_2$—O—$CH_3$ and Z is —CO—$CH_3$, —CO—O—$C_2H_5$, —CO—NH-phenyl, —CO—NH—$C_2H_5$, —CO—$C_2H_5$, —CO-phenyl or —$CH_3$.

2. Compounds according to claim 1, wherein $R^1$ is selected from the group consisting of a methyl and an ethyl group.

3. Compounds according to claim 1 or 2, characterized in that $R^2$ is selected from the group consisting of an alkyl group containing 1–6 carbon atoms, an acyl residue containing 1–6 carbon atoms, or a residue —$CONHR^4$ or —$COOR^4$, where $R^4$ is selected from the group consisting of a hydrogen atom or an alkyl or aryl residue containing 1–6 carbon atoms.

4. Compounds according to claim 1 or 2, characterized in that $R^3$ is selected from the consisting of an alkyl group containing 1–6 carbon atoms.

5. Compounds according to claim 1, characterized in that $R^3$ is selected from the group consisting of a residue —$(CH_2)_n$—$CH_2X$, where n=0, 1, or 2, X is selected from the group consisting of a fluorine, chlorine, bromine, or iodine atom, a cyano, azide, or rhodano group, a residue $OR^5$ or $SR^5$, wherein $R^5$ is selected from the group consisting of an alkyl residue containing 1–6 carbon atoms, or an acyl residue containing 1–6 carbon atoms.

6. Compounds according to claim 1 or 2, characterized in that $R^3$ is selected from the group consisting of a residue $OR^5$, $R^5$ is selected from the group consisting of an alkyl residue containing 1–6 carbon atoms, or an acyl residue containing 1–6 carbon atoms.

7. Compounds according to claim 1 or 2, characterized in that $R^3$ is selected from the group consisting of a residue —$(CH_2)_o$—$CH=CH(CH_2)_p$—$R^6$, where o=0, 1, 2 or 3 and p=0, 1, or 2 and $R^6$ is selected from the group consisting of an alkyl group containing 1–6 carbon atoms, an alkoxy or acyloxy group containing 1–6 carbon atoms.

8. Compounds according to claim 1 or 2, characterized in that $R^3$ is selected from the group consisting of a residue —$(CH_2)_q C \equiv CR^7$, where q=0, 1, or 2 and $R^7$ is selected from the group consisting of an alkyl residue containing 1–6 carbon atoms, or an acyl residue containing 1–6 carbon atoms.

9. Compounds according to claim 1 or 2, characterized in that Z is selected from the group consisting of an alkyl residue containing 1–6 carbon atoms, an acyl residue containing 1–6 carbon atoms, a residue —$CONHR^4$ or —$COOR^4$, where $R^4$ is selected from the group consisting of a hydrogen atom, an alkyl or an aryl residue containing 1–6 carbon atoms.

10. Compounds according to claim 1, selected from the group consisting of:

11β-[4-(hydroximinomethyl)phenyl]-17β-hydroxy-17α-methoxymethyl-estra-4,9-diene-3-on, 11β-[4-(hydroximinomethyl)phenyl]-17β-hydroxy-17α-ethoxymethyl-estra-4,9-diene-3-on, 11β-[4(hydroximinomethyl)phenyl]-17β-hydroxy-17α-n-propoxymethyl-estra-4,9-diene-3-on,
11β-[4-(hydroximinomethyl)phenyl]-17β-hydroxy-17α-i-propoxymethyl-estra-4,9-diene-3-on,
11β-[4-(hydroximinomethyl)phenyl]-17β-methoxy-17α-methoxymethyl-estra-4,9-diene-3-on,
11β-[4-(hydroxyiminomethyl)phenyl]-17β-methoxy-17α-ethoxymethyl-estra-4,9-diene-3-on,
11β-[4-(hydroxyiminomethyl)phenyl]-17β-hydroxy-17α-(3-hydroxyprop-1-in-yl)-estra-4,9-diene-3-on,
11β-[4-(hydroxyiminomethyl)phenyl]-17β-methoxy-17α-(3-hydroxyprop-1-in-yl)-estra-4,9-diene-3-on,
11β-[4-(hydroximinomethyl)phenyl]-17β-hydroxy-17α-Z-(3-hydroxypropenyl)-estra-4,9-diene-3-on,
11β-[4-(hydroximinomethyl)phenyl]-17β-methoxy-17α-Z-(3-hydroxypropenyl)-estra-4,9-diene-3-on,
17α-chloromethyl-11β-[4-hydroximinomethyl)phenyl]-17β-hydroxy-estra-4,9-diene-3-on,
17α-chloromethyl-11β-[4-hydroximinomethyl)phenyl]-17β-methoxy-estra-4,9-diene-3-on,
17α-cyanomethyl-11β-[4-hydroximinomethyl)phenyl]-17β-hydroxy-estra-4,9-diene-3-on,
17α-cyanomethyl-11β-[4-hydroximinomethyl)phenyl]-17β-methoxy-estra-4,9-diene-3-on,
17α-azidemethyl-11β-[4-hydroximinomethyl)phenyl]-17β-methoxy-estra-4,9-diene-3-on,
11β-[4-(hydroximinomethyl)phenyl]-17β-methoxy-17α-methylthiomethyl-estra-4,9-diene-3-on,
11β-[4-(methyloximinomethyl)phenyl]-17β-methoxy-17α-methoxymethyl-estra-4,9-diene-3-on, and
11β-[4-(hydroximinomethyl)phenyl]-17β-ethoxy-17α-ethoxymethyl-estra-4,9-diene-3-on.

11. A method for producing the compounds according to claim 1 and their pharmaceutically acceptable salts, characterized in that a compound of general formula II

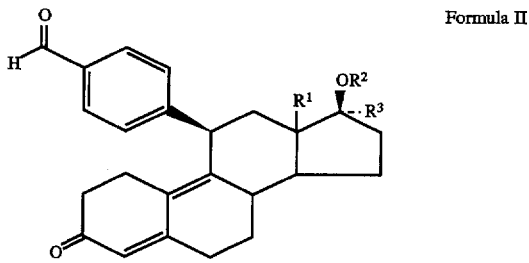

Formula II wherein
$R^1$ is selected from the group consisting of a hydrogen atom or alkyl residue containing 1–6 carbon atoms,
$R^2$ is selected from the group consisting of a hydrogen atom, an alkyl, aryl, aralkyl, or alkylaryl group containing 1–10 carbon atoms, an acyl residue containing 1–10 carbon atoms, or a residue —CONHR$^4$ or —COOR$^4$,
where $R^4$ is selected from the group consisting of a hydrogen atom, an alkyl, aryl, aralkyl, or alkylaryl residue containing 1–10 carbon atoms,
$R^3$ is selected from the group consisting of a hydrogen atom, an alkyl, aryl, aralkyl, or alkylaryl residue containing 1–10 carbon atoms,
a residue —(CH$_3$)$_n$—CH$_2$X,
where n=0, 1, or 2, X is selected from the group consisting of a hydrogen atom, an alkyl, aryl, aralkyl, or alkaryl residue containing 1–10 carbon atoms, a fluorine, chlorine, bromine, or iodine atom, a cyano, azide, or rhodano group, a residue OR$^5$ or SR$^5$, $R^5$ is selected from the group consisting of a hydrogen atom, an alkyl, aryl, aralkyl, or alkaryl residue containing 1–10 carbon atoms, or an acyl residue containing 1–10 carbon atoms,
a residue OR$^5$,
in which $R^5$ has the meaning specified above,
a residue —(CH$_2$)$_n$—CH=CH(CH$_2$)$_p$—R$^6$,
where o=0, 1, 2, or 3 and p=0, 1, or 2, and $R^6$ is selected from the group consisting of a hydrogen atom, an alkyl, aryl, aralkyl, or alkyaryl group containing 1–10 carbon atoms, a hydroxyl group, an alkoxy or acyloxy group containing 1–10 carbon atoms,
a residue —(CH$_2$)$_q$C≡CR$^7$,
where q=0, 1, or 2, and $R^7$ is selected from the group consisting of a hydrogen atom, a fluorine, chlorine, bromine, or iodine atom, an alkyl, aryl, aralkyl, or alkyaryl residue containing 1–10 carbon atoms, or an acyl residue containing 1–10 carbon atoms,
is reacted with a compound of the general formula IIa

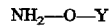 Formula IIa where Y is selected from the group consisting of a hydrogen atom, an alkyl residue containing 1–10 carbon atoms, an acyl residue containing 1–10 carbon atoms, or a residue
—CONHR$^4$ or COOR$^4$,
where $R^4$ is selected from the group consisting of a hydrogen atom, an alkyl, aryl, aralkyl, or alkylaryl residue containing 1–10 carbon atoms,
and where the compound of the general formula IIa is present, if required, in the form of such compound, or from which the compound of the general formula IIa is released under the selected conditions of the reaction,
the hydroxyl amine group, if present, is esterified or etherified, and the resulting compound salified.

12. The method according to claim 11, characterized in that the compounds of general formula II are reacted with the compounds of general formula IIa in equimolar quantities.

13. Compounds in accordance with claim 1, and salts thereof, produced through the process of reacting compounds of a general formula II:

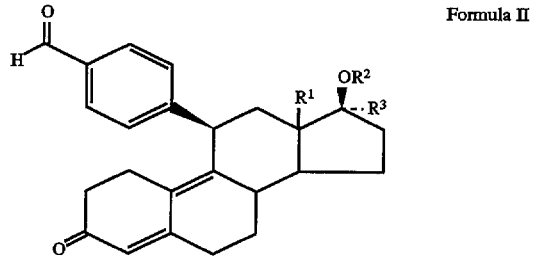

Formula II wherein
$R^1$ is selected from the group consisting of a hydrogen atom or alkyl residue containing 1–6 carbon atoms,
$R^2$ is selected from the group consisting of a hydrogen atom, an alkyl, aryl, aralkyl, or alkylaryl group containing 1–10 carbon atoms, an acyl residue containing 1–10 carbon atoms, or a residue —CONHR$^4$ or —COOR$^4$,
where $R^4$ is selected from the group consisting of a hydrogen atom, an alkyl, aryl, aralkyl, or alkylaryl residue containing 1–10 carbon atoms, $R^3$ is selected from the group consisting of a hydrogen atom, an alkyl, aryl, aralkyl, or alkylaryl residue containing 1–10 carbon atoms, a residue —$(CH_3)_n$—$CH_2X$,
  where n=0, 1, or 2, X is selected from the group consisting of a hydrogen atom, an alkyl, aryl, aralkyl, or alkaryl residue containing 1–10 carbon atoms, a fluorine, chlorine, bromine, or iodine atom, a cyano, azide, or rhodano group, a residue $OR^5$ or $SR^5$,
  $R^5$ is selected from the group consisting of a hydrogen atom, an alkyl, aryl, aralkyl, or alkaryl residue containing 1–10 carbon atoms, or an acyl residue containing 1–10 carbon atoms, a residue $OR^5$,
  in which $R^5$ has the meaning specified above, a residue —$(CH_2)_n$—CH=CH$(CH_2)_p$—$R^6$,
  where o=0, 1, 2, or 3 and p=0, 1, or 2, and $R^6$ is selected from the group consisting of a hydrogen atom, an alkyl, aryl, aralkyl, or alkyaryl group containing 1–10 carbon atoms, a hydroxyl group, an alkoxy or acyloxy group containing 1–10 carbon atoms, a residue —$(CH_2)_q$C≡$CR^7$,
  where q=0, 1, or 2, and $R^7$ is selected from the group consisting of a hydrogen atom, a fluorine, chlorine, bromine, or iodine atom, an alkyl, aryl, aralkyl, or alkyaryl residue containing 1–10 carbon atoms, or an acyl residue containing 1–10 carbon atoms, with a compound of the general formula IIa $$NH_2—O—Y \qquad \text{Formula IIa}$$

where Y is selected from the group consisting of a hydrogen atom, an alkyl residue containing 1–10 carbon atoms, an acyl residue containing 1–10 carbon atoms, or a residue —$CONHR^4$ or $COOR^4$,
  where $R^4$ is selected from the group consisting of a hydrogen atom, an alkyl, aryl, aralkyl, or alkylaryl residue containing 1–10 carbon atoms.

14. Pharmaceutical compositions, characterized in that they contain at least one compound according to claim 1.

15. A pharmaceutical composition, comprising a pharmaceutically effective concentration of a compound according to claim 1, or salts or mixtures thereof, in a pharmaceutically acceptable carrier.

* * * * *